(12) United States Patent
Kon et al.

(10) Patent No.: US 6,531,482 B1
(45) Date of Patent: *Mar. 11, 2003

(54) METHOD AND COMPOSITIONS FOR MAINTAINING GLOMERULAR FILTRATION RATE WHILE INHIBITING EXTRACELLULAR MATRIX ACCUMULATION

(75) Inventors: Valentina Kon, Nashville, TN (US); Agnes Fogo, Mount Juliet, TN (US); Iekuni Ichikawa, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/542,314

(22) Filed: Apr. 4, 2000

Related U.S. Application Data

(63) Continuation of application No. 08/130,134, filed on Aug. 6, 1998, now abandoned, which is a continuation-in-part of application No. 08/920,082, filed on Aug. 26, 1997, now abandoned, which is a continuation of application No. 08/468,242, filed on Jun. 6, 1995, now Pat. No. 5,677,312, which is a continuation of application No. 08/279,901, filed on Jul. 25, 1994, now Pat. No. 6,512,580, which is a continuation of application No. 07/942,756, filed on Sep. 9, 1992, now abandoned.

(51) Int. Cl.⁷ .............................................. A61K 31/44
(52) U.S. Cl. ........................................ 514/303; 574/300
(58) Field of Search ............................... 514/303, 300

(56) References Cited

U.S. PATENT DOCUMENTS

| | | | |
|---|---|---|---|
| 5,049,565 A | 9/1991 | Chen et al. | 514/302 |
| 5,087,702 A | 2/1992 | Chen et al. | 546/118 |
| 5,210,079 A | 5/1993 | Carini et al. | 514/94 |

FOREIGN PATENT DOCUMENTS

| | | | | |
|---|---|---|---|---|
| WO | WO 92/10182 | 6/1992 | .......... | A61K/31/41 |

OTHER PUBLICATIONS

Chang et al. *FASEB* 5(Part 111):6993 (Abstr) 1991.
Kon et al. "Bradykinin causes selective efferent arteriolar dilation during angiotensin I converting enzyme inhibition", *Kidney Internat'l* 44:545–550, Sep. 1993.
Peten et al. "High dose ACE inhibitor (ACEI) or ANGII receptor antagonist (ANTII RI) therapy does not improve glomerulosclerosis (GS) in mice transgenic for growth hormone (GH MICE)", *J. Am. Soc. Nephrol.* Abstract vol. 4(3), p. 780, Sep. 1993.
Kakinuma et al. "Blood pressure–independent effect of angiotensin inhibition on vascular lesions of chronic renal failure", *Kidney Internat'l* 42(1):46–55, Jul. 1992.
Chan et al. "Renal–specific actions of angiotensin II receptor antagonism in the anesthetized dog" *Am. J. Hypertens.* 5:354–360, Jun. 1992.

Kivlighn et al. "Antihypertensive efficacy and effects on renal function of L–158,809: A nonpeptide orally active angiotension II antagonist" *Hypertension* Abstract 19(1):I–135, Jan. 1992.
Kivlighn et al. "Antihypertensive efficacy and effects on renal function in the conscious spontaneously hypertensive rat (SHR)" *FASEB Journal* Abstract vol. 5(5), p. A1576, Mar. 19, 1991.
Bovee et al. "Effects of the nonpeptide angiotensin II receptor antagonist DuP 753 on blood pressure and renal functions in spontaneously hypertensive PH dogs", *Am. J. Hypertens.* 4:327S–333S, Apr. 1991.
Takeda, et al. *Kidney International*, 42:1713–1719, 1992.
Fogo et al. *Kidney International* 42:770–774, 1992.
Awazu et al. *J. Amer Soc. Nephrology*, 1:1253–1258, 1991.
Kon and Badr *Kidney International*, 40:1–12, 1991.
Kon et al. *Kidney International*. 37:1487–1491, 1990.
Burnier et al. "Salt–Dependent Renal Effects of an Angiotensin II Antagonist in Healthy Subjects" *Hypertension* 22:339–347, 1993.
Tsunoda et al. "Hypertensive Effect of Losartan, a Nonpeptide Angiotensin II Receptor Antagonist, in Essential Hypertension" *Am J of Hypertens* 6(1):28–32, Jan. 1993.
Weber, Michael A. "Clinical Experience With the Angiotensin II Receptor Antagonist Losartan" *Am J Hypertens* 5(12) Part 2:247S–251S, Dec. 1992.
Duncia et al. The Discovery of DuP 753, a Potent, Orally Active Nonpeptide Angiotensin II Receptor Antagonist, *Med Res Rev* 12(2):149–91, Mar. 1992.
Mimran et al. "Converting Enzyme Inhibitors and Renal Function in Essential and Renovascular Hypertension" *Am J of Hypertens* 4(1) Part 2:7S–14S, Jan. 1991.
Prescott et al. "Angiotensin–Converting Enzyme Inhibitor Versus Angiotensin II, At₁ Receptor Antagonist: Effects on Smooth Muscle Cell Migration and Proliferation After Balloon Catheter Injury" *Am J of Pathology* 139(6):1291–1296, Dec. 1991.

(List continued on next page.)

Primary Examiner—Jerome D. Goldberg
(74) Attorney, Agent, or Firm—Needle & Rosenberg, P.C.

(57) ABSTRACT

This invention provides a method of and compositions for increasing or maintaining glomerular filtration rate while preserving renal structure in a patient comprising administering an angiotensin II type 1 vascular receptor antagonist to the patient, independent of its effects on systemic blood pressure. The invention provides that, by administering the AII type 1 receptor antagonist, blood flow to the kidney can be improved without sacrificing intraglomerular pressure and therefore glomerular filtration and that even with this enhanced glomerular pressure and filtration, renal structure is preserved. Also provided is a method of screening AII type 1 receptor antagonists for the ability to maintain or increase glomerular filtration rate while decreasing mesangial matrix accumulation comprising the steps of administering the antagonist in an animal model characterized by decreased glomerular filtration rate and increased mesangial matrix accumulation and selecting the compounds that increase glomerular filtration rate while decreasing mesangial matrix accumulation.

12 Claims, 3 Drawing Sheets

OTHER PUBLICATIONS

Siegl et al. "In Vitro Pharmacology of a Highly Potent and Selective Nonpeptide Angiotensin II (AII) Receptor Antagonist: L–158, 809" *Antihypertensive Drugs I*, Abstract No. 6994, A1576, 1991.

Kamper, Anne–Lise "Angiotensin Converting Enzyme (ACE) Inhibitors and Renal Function" *Drug Safety* 6(5):361–370, 1991.

Chiu et al. "Nonpeptide Angiotensin II Receptor Antagonists. VII. Cellular and Biochemical Pharmacology of DuP 753, an Orally Active Antihypertensive Agent" *J Pharmacol Exp Ther* 252(2):711–718, Feb. 1990.

Hricik et al. "Angiotensin–Converting Enzyme Inhibitor–Induced Renal Failure: Causes, Consequences, and Diagnostic Uses" *J. Am. Soc. Nephrol.* 1(6):845–858, 1990.

Kalra et al. "Renovascular Disease and Renal Complications of Angiotensin–Converting Enzyme Inhibitor Therapy" *Quarterly Journal of Medicine* 77(282):1013–1018, Oct. 1990.

Speirs et al. "Postmarketing Surveillance of Enalapril. II: Investigation of the Potential Role of Enalapril in Deaths with Renal Failure" *BMJ* 297(6652):830–832, Oct. 1988.

Slaughter et al. "Canine Essential Hypertension: Probable Mode of Inheritance" *J. of Hypertens*, 4(Suppl. 5):S170–S171, 1986.

Hostetter et al. "Cardiorenal Hemodynamics and Sodium Excretion in Rats with Myocardial Infarction" *Am J Physiol*, 245(1):H98–103, Jul. 1983.

Brenner et al. "Dietary Protein Intake and the Progressive Nature of Kidney Disease: The Role of Hemodynamically Mediated Glomerular Injury in the Pathogenesis of Progressive Glomerular Sclerosis in Aging, Renal Ablation, and Intrinsic Renal Disease" *N Engl J of Med*, 307(11):652–659, Sep. 9, 1982.

METHOD AND COMPOSITIONS FOR MAINTAINING GLOMERULAR FILTRATION RATE WHILE INHIBITING EXTRACELLULAR MATRIX ACCUMULATION

This application is a Con of Ser. No. 09/130,134 filed Aug. 6, 1998 now abn. which is a Cip of Ser. No. 08/920,082 filed Aug. 26, 1997 now abn. which is a Con of Ser. No. 08/468,242 filed Jun. 6, 1995 now U.S. Pat. No. 5,677,312 which is a Con of Ser. No. 08/279,901 filed Jul. 25, 1994 now U.S. Pat. No. 6,512,580 which is a Con of Ser. No. 07/942,756 filed Sep. 9, 1992 now abn.

This invention was made with government support under Grants DK-42159, DK-39547, DK44757 and DK-37869 from the National Institutes of Health. The U.S. Government may have certain rights in this invention.

Throughout this application various publications are referenced by numbers within parentheses. Full citations for these publications may be found at the end of the specification immediately preceding the claims. The disclosures of these publications in their entireties are hereby incorporated by reference into this application in order to more fully describe the state of the art to which this invention pertains.

BACKGROUND OF THE INVENTION

Angiotensin II (AII) is now known to act on the systemic vasculature and at several sites within the renal microcirculation with effects on vascular tone and vascular growth and extracellular matrix accumulation (1–6, 40). Angiotensin I converting enzyme inhibitor (ACEI) has been used as a primary tool to control hypertension, increase organ blood flow and preserve organ structure. However, while ACEI causes vasodilation, including within the renal circulation, its specific effects, to decrease resistance of both glomerular afferent and efferent arterioles, can reduce glomerular capillary pressure and therefore filtration. The renin angiotensin system (RAS) has been postulated to be linked to other vasoactive substances, notably bradykinin, which may account for part of ACEI-induced vasodilatation (7–12). Assessment of the specific effects of endogenous AII on the renal circulation has been limited by this uncertain non-specific action of ACEI, and also by the partial agonist effects of previously available AII analogues. Recently, the availability of both a specific nonpeptide AII type 1 receptor antagonist (AIIRA) which lacks agonist effects (13, 14), and a specific bradykinin receptor antagonist (15) has circumvented these difficulties. These developments are important, since it is frequently necessary to inhibit RAS effects in patients, including vasoconstriction, vascular growth and extracellular matrix accumulation.

Thus, there is a great need for a method of inhibiting RAS while maintaining or increasing GFR levels and protecting the kidney from structural injury. The invention provides that this can be accomplished by antagonizing AII type 1 vascular receptor in a patient. Further, this invention provides that these beneficial effects on the kidney can be accomplished independently of AII type 1 vascular receptor antagonist effects on systemic blood pressure or other cardiac pathologies.

SUMMARY OF THE INVENTION

This invention provides a method of and compositions for increasing or maintaining glomerular filtration rate while preserving renal structure in a patient comprising administering an angiotensin II type 1 vascular receptor antagonist to the patient, independent of its effects on systemic blood pressure. The invention provides that, by administering the AII type 1 receptor antagonist, blood flow to the kidney can be improved without sacrificing intraglomerular pressure and therefore glomerular filtration and that even with this enhanced glomerular pressure and filtration, renal structure is preserved. Also provided is a method of screening AII type 1 receptor antagonists for the ability to maintain or increase glomerular filtration rate while decreasing mesangial matrix accumulation comprising the steps of administering the antagonist in an animal model characterized by decreased glomerular filtration rate and increased mesangial matrix accumulation and selecting the compounds that increase glomerular filtration rate while decreasing mesangial matrix accumulation.

DETAILED DESCRIPTION OF THE INVENTION

Figure 1A:
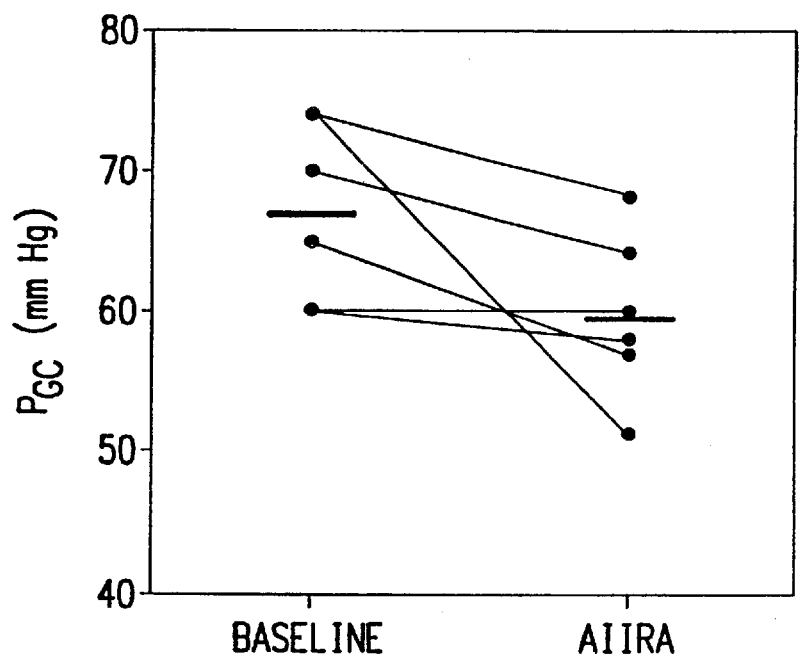
FIG. 1 shows individual glomerular capillary pressure ($P_{GC}$) values in Group II AWD rats during baseline and following angiotensin II receptor antagonist (AIIRA) and angiotensin I converting enzyme (ACEI) showing markedly greater fall in $P_{GC}$ with ACEI.

This invention provides a method of maintaining or increasing glomerular filtration rate (GFR) while inhibiting mesangial matrix accumulation in a patient. The method comprises administering an amount of an AII type 1 vascular receptor antagonist that would maintain or increase GFR while preserving renal structure in the patient. The invention provides that, by administering the AII type 1 receptor antagonist, blood flow to the kidney can be improved without sacrificing intraglomerular pressure and therefore glomerular filtration, and that even with this enhanced glomerular pressure and filtration, renal structure is preserved. One antagonist which has proven appropriate is L-158,809 (5,7-dimethyl-2-ethyl-3-[[2'-(1H-tetrazol-5yl)[1,1']-biphenyl-4-yl]-methyl]-3H-imidazo[4,5-b]pyridine). Other appropriate antagonists include DuP 753 and any non-peptide AII type 1 receptor antagonist now known or later discovered. Such antagonists can be screened and selected by the methods provided herein.

The amount of an AII type 1 vascular receptor antagonist that can maintain or increase GFR and inhibit mesangial matrix accumulation may not be related to pressor dose. As used herein, the "pressor dosage" means the dosage of antagonist one would administer to normalize hypertension. In patients with an accumulation of mesangial matrix or a history of renal failure, the preferred dosage can be greater than the pressor dosage. Any pharmaceutically acceptable water or lipid soluble carrier would be appropriate as a carrier for antagonist compositions in doses greater than the pressor dosage.

AII type 1 receptor antagonist is administered to patients in whom systemic/renal vasodilation is desired without compromising glomerular filtration. Such patients would include those suffering from hypertension with or without renal structural injury in whom maintenance or increase in GFR can be accomplished with control of systemic hypertension and inhibition of progressive renal structural injury. Such patients would also include those with ischemic cardiac disease, cardiac dysfunction following infarction, and cardiomyopathy, whether or not these patients have systemic hypertension. Therefore, the invention allows for the intentional simultaneous treatment of systemic hypertension and function and structure of the kidneys utilizing an AII type 1 receptor antagonist. As used herein, "hypertensive" means a blood pressure above 150/90 mm Hg in adults which is above the normal range of 120/80 mm Hg. The range for hypertension in children varies and is dependent on age and body size.

The invention also provides a method of screening AII type 1 receptor antagonists for the ability to maintain or increase GFR while decreasing mesangial matrix accumulation. The method comprises the steps of administering the antagonist in an animal model characterized by decreased GFR and increased mesangial matrix accumulation and selecting the compounds that maintain or increase GFR while decreasing mesangial matrix accumulation. One such model to evaluate effects on glomerular filtration, the AWD rat model, is set forth in the Examples. A model to examine effects on glomerular filtration and structure chronically, the renal ablation model, is described in Reference 40.

RAS is important in regulating vasomotor tone in the systemic and organ vasculatures. Interruption of the RAS to decrease vasoconstriction is often a therapeutic goal, but is associated with variable effects on GFR (6, 17, 21–30). Studies in the AWD rat, a model characterized by hypoperfusion and hypofiltration with activation of the RAS, examined these issues. Antagonizing AII actions by inhibition of converting enzyme vasodilated the systemic and renal circulations; systemic blood pressure decreased and renal plasma flow increased, however, there was no improvement in GFR. Analysis of the microcirculatory hemodynamics revealed that arteriolar resistances decreased, particularly in the efferent arteriole, which contributed to the increase in $Q_A$. However, the efferent arteriolar dilatation also caused a profound fall in $P_{GC}$ (by 16 mm Hg), which offset the effects of increases in $Q_A$ and $K_f$, and resulted in no improvement in single nephron glomerular filtration rate (SNGFR). These findings are in accord with reports that inhibition of RAS can increase, decrease, or leave unchanged the rate of filtration, and emphasize that the net effect on GFR depends upon the balance of AII's effects on $R_A$, $R_E$ and $K_f$ (6, 16, 17, 24). In more severe hemodynamic decompensation, glomerular filtration may be critically dependent on heightened RAS which promotes efferent arteriolar maintenance of $P_{GC}$ and GFR. Removal of this critical compensation then leads to a fall in GFR (17). This notion is supported by the observation that decreased GFR and azotemia develop in patients on ACEI with superimposed circulatory stress such as blood loss, addition of diuretics or other fluid loss, which overwhelms already maximal compensation by RAS (22, 23, 25–28, 31). It should be emphasized that hypofiltration occurs even in the absence of profound systemic hypotension (22, 31). Further, for similar decrease in systemic blood pressure, hypofiltration occurs more frequently when RAS is inhibited compared with systemic vasodilatation achieved with maneuvers not involving RAS inhibition. These findings then implicate renal, rather than systemic, changes which are responsible for decreasing filtration.

Figure 1B:
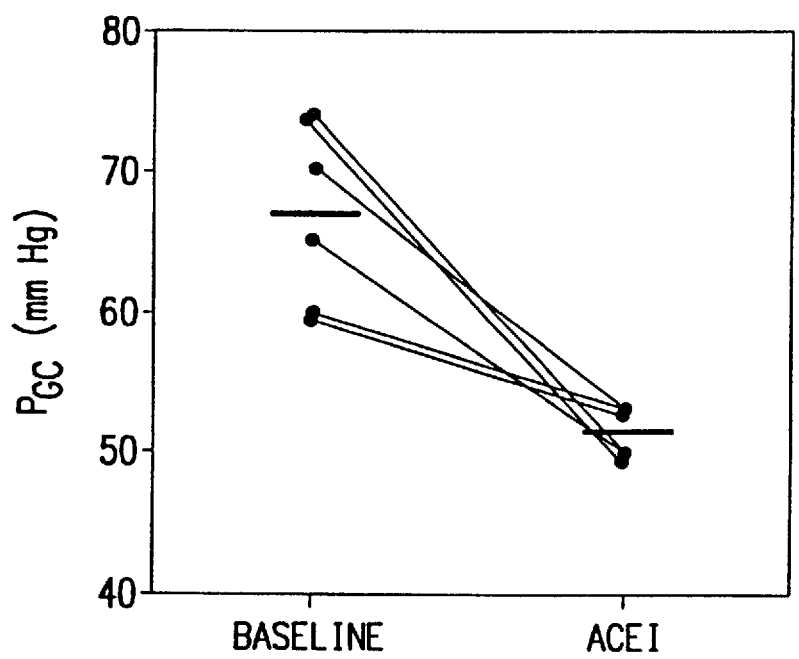

The effects of a specific AII type I receptor antagonist (AIIRA) were examined, as set forth in the following Examples. The angiotensin type I receptor is one of two angiotensin receptor types identified in humans, and is the subtype that mediates cardiovascular actions of AII (32). The renal distribution of the mRNA of this receptor was examined in our recent in situ hybridization studies. No signal was detected in interlobular arteries while this signal was prominent in vessels regulating blood flow and filtration, including both afferent and efferent arterioles and the mesangium (33). In contrast to ACEI, the present data shows that antagonizing type I AII vascular receptor caused renal vasodilatation, which was accompanied by a striking increase in filtration (Table 1 and FIGS. 1 and 2). This difference was apparent between periods within an animal and also between groups. While the magnitude of decrease in systemic blood pressure and increase in $Q_A$ were similar, antagonism of AII with a receptor antagonist resulted in lesser reduction in efferent arteriolar tone than inhibition of ACE (Table 1 and FIG. 3). This is reflected by the changes in $P_{GC}$. Thus, although systemic blood pressures was decreased to the same degree by both ACEI and AIIRA, ACEI caused $P_{GC}$ to fall by 16 mm Hg, compared with 7 mm Hg fall following AIIRA.

Differences in the microcirculatory hemodynamic changes after interrupting the RAS at these different sites of action, i.e. at the interaction of ligand and type I receptor vs. inhibition of conversion of angiotensin I to AII, demonstrate that other AII effects or non-AII actions contribute, at least in part, to the dyssynchrony between renal vasodilatation and filtration following ACEI. In this regard, circulating levels of AII modulate expression of the genes of the RAS, including renin, angiotensinogen and ACE (34). Since circulating AII levels are higher after AIIRA than ACEI treatment (35), this higher levels of unbound AII can interact with other vasoactive substances, or bind with type II receptor or other angiotensin binding proteins. The possibility of additional, non-AII effects (e.g. interaction with vasodilators) is of interest in view of the previous observation that rats with renal hypoperfusion because of congestive heart failure and AWD developed a paradoxical fall in efferent arteriolar tone in response to superimposed reduction in renal perfusion pressure (17). In this setting, the expected renal vasodilatation is postulated to reflect attenuation of AII actions. However, the observations demonstrate that the failure to increase or actually even decreasing GFR during such renal vasodilatation is not simply attenuation of AII effects, rather it is an active vasodilatation.

Some vasodilators are associated with RAS, including bradykinin, endothelium-derived relaxing factor and prostaglandins, although the data demonstrates that the latter does not have a major role in this regard. Of note, angiotensin I converting enzyme inhibitors inactivate kininase II, a kinin-degrading enzyme which would result in accumulation of bradykinin. Bradykinin's contribution to ACEI-induced vasodilatation has been controversial (8–12, 36–38). There is accumulating evidence that kinins play an important role in regulating renal function, including recent evidence that kinins can be formed in the renal circulation. This is of particular relevance since among isolated rabbit interlobular, efferent and afferent arteriolar preparations, bradykinin caused marked vasodilatation only in the efferent arteriole (39). Bradykinin's role in the ACEI-induced vasodilatation was investigated, in particular whether the dramatic decrease in efferent arteriolar resistance is related to the enhanced bradykinin activity. The data in animals treated with ACEI clearly show that antagonizing bradykinin opposed the decrease in efferent arteriolar resistance effected by converting enzyme inhibition (FIG. 3). This in turn caused an elevation in glomerular pressure which was pivotal in increasing GFR.

Interruption of the RAS by ACEI is now used in many circumstances to lower blood pressure, to effect afterload reduction, decrease proteinuria and also to forestall chronic deterioration in renal function. While vasodilatation and renal sparing is a desirable therapeutic end point in the kidney, a decrease in vascular resistance can cause not only renal vasodilatation but also may decrease glomerular capillary pressure, and therefore remove an important compensatory mechanism to maintain GFR. These data show that renal vasodilatation following inhibition of angiotensin I converting enzyme is at least in part related to bradykinin. These data further indicate that in conditions where high $P_{GC}$ is crucial in maintaining GFR, activation of bradykinin by ACEI can precipitate severe compromise in GFR, and that this untoward effect can be largely avoided with a more specific vasodilator for antagonism of AII effects.

EXAMPLES

Experiments were done in adult male Munich-Wistar rats. All animals were deprived of water for 48 hours (acute water deprivation, AWD), a model characterized by hypoperfusion, hypofiltration and activated RAS (6, 16, 17). Renal function was then assessed as described in detail below. AWD decreased the body weight, on average, by 15%.

Group I AWD treated with ACEI (n=6). Rats were prepared for micropuncture as previously described (6, 16, 17). Briefly, under Inactin anesthesia (70 mg/kg body wt i.p., BYK, Konstanz, Germany), trachcotomy was performed, and indwelling polyethylene catheters were inserted into the femoral artery and vein and the jugular vein for blood sampling, monitoring of systemic blood pressure, and infusion of inulin and plasma, as previously described (6, 16, 17). Determinations of SNGFR, hydraulic pressures in glomerular capillaries ($P_{GC}$), proximal tubules ($P_T$), and efferent arterioles were made. Femoral arterial ($C_A$) and efferent arteriolar ($C_E$) plasma protein concentrations were also obtained, permitting calculation of glomerular plasma flow rate ($Q_A$) and ultrafiltration coefficient ($K_f$), as well as resistances of afferent ($R_A$) and efferent ($R_E$) arterioles. Colloid osmotic pressures of plasma entering and leaving the glomerular capillaries were estimated from $C_A$ and $C_E$ using derivations of Deen et al. (18, 19). Details of the analytical procedure for inulin in plasma and nanoliter tubule fluid samples, and that for $C_A$ and $C_E$ are described elsewhere (18, 19). After baseline measurements and collections, each rat was treated with ACEI (enalapril, 0.3 mg/kg i.v. bolus, then 0.3 mg/hr continuous i.v. infusion). After 60 minutes, micropuncture measurements were repeated.

Group II AWD treated with AIIRA and ACEI (n=6). Rats were prepared as in Group I except that, after baseline measurements, AIIRA (4 mg/kg body wt i.v. as bolus and then as continuous infusion, L-158,809, Merek, Sharp & Dohme), a specific type I angiotensin receptor II antagonist, was started. Renal micropuncture measurements were performed 1 hour after AIIRA was started. AIIRA was then discontinued and ACEI was infused as in Group I with repeat micropuncture measurements after 1 hour. Since the AIIRA has half life exceeding 6 hours in the rat (14) and effects in the ACEI period may in part reflect alterations of the RAS after receptor inhibition, we studied separate groups of animals treated with either ACEI or AIIRA.

Groups IIIA and B, AWD+Furosemide, treated with ACEI (n=6) or AIIRA (n=6). To confirm differences in renal function between ACEI versus AIIRA under conditions with extreme stimulation of the RAS, we studied animals that received furosemide in addition to water deprivation. Furosemide (2.5 mg/kg body wt i.p.) was administered at the start of water deprivation and again the next day which was at least 24 hours prior to micropuncture/clearance studies to avoid confounding effects of furosemide activation of tubuloglomerular feedback. Following surgical preparation, baseline clearance studies were obtained as previously described (6, 16, 17). The animals were then treated with either ACEI (Group IIIA, n=6) or AIIRA (Group IIIB, n=6), as described above. Measurements were repeated 60 minutes later.

Group IVA and B, AWD+Furosemide, treated with ACEI+bradykinin receptor antagonist, Hoe (n=9), or Hoe (n=6). These animals were prepared as Group IIIA (baseline, then ACEI) but, in addition, a third period of study was added. Thus, during ACEI treatment renal hemodynamic studies were performed, and then a newly developed bradykinin antagonist was added (0.1 mg/kg body wt i.v. bolus and s.c, Hoe-140, HOECHT, Frankfurt, Germany). Micropuncture measurements were then performed. The bradykinin antagonist has previously been shown to be highly protective in vivo, completely preventing bradykinin-induced systemic hypotension after 1 hour and with only minimal hypotension (~5% decrease in blood pressure) 2 hours following subcutaneous administration (15). Group IVB rats were treated identically, except that no ACEI was given. The same dose of Hoe-140 was administered before measurement of renal clearances at 1 hour.

To assess a potential role for prostaglandins in the effects of ACEI versus AIIRA, a separate group was pretreated with indomethacin, 2 mg/kg body wt/hr i.v. Following micropuncture/clearance studies, the animals received either ACEI (n=4) or AIIRA (n=4) as above, and renal studies were repeated.

Group I, AWD treated with ACEI. Whole kidney GFR, SNGFR, and $Q_A$ (0.46±0.07 ml/min, 16.2±1.9 nl/min, and 53±6 nl/min, respectively) were characteristic of the hypoperfusion/hypofiltration pattern of renal hemodynamics and distinct from normal cuvolemic rats (6, 16, 17). These parameters reflect higher than normal afferent and efferent arteriolar resistances (0.402±0.044 mm Hg·min/nl and 0.543±0.085, respectively). Inhibition of angiotensin I converting enzyme activity decreased MAP from 107±6 mm Hg to 94±5, and caused renal dilatation. Thus, $Q_A$ values increased to 102±24 nl/min, due to a decrease in arteriolar resistances, particularly of the efferent arteriole (from 0.543±0.085 mm Hg·min/nl to 0.235±0.048, p<0.025). The fall in $R_E$ was apparent in the profound decrease in the intraglomerular pressure; $P_{GC}$ fell from the higher than typical cuvolemic value of 65±2 mm Hg to 49±1 (p<0.005). As expected, inhibition of AII activity caused an increase in the value of $K_f$ [1.020±0.240 nl/(min·mm Hg) vs. 2.700±0.600, p<0.025]. The cumulative effect of these changes was the lack of consistent improvement in filtration (GFR 0.46±0.07 vs. 0.54±0.06, p NS). In the next set of experiments, the mechanism of AII's actions on the glomerular microcirculation was explored by interrupting the RAS at different sites in the same animals.

Group II AWD treated with AIIRA and ACEI. Group II rats were prepared identically to Group I and again showed the typical renal hypoperfusion of AWD. These data are shown in Table 1 and FIG. 1. In contrast to Group I ACEI-treated rats, both GFR (p<0.05) and SNGFR (p<0.025) increased significantly with AIIRA. Evaluation of individual parameters that affect filtration revealed vasodilatation, particularly due to a fall in efferent arteriolar resistance (p<0.05). Of note, while $P_{GC}$ fell from 67±3 mm Hg to 60±2 (p<0.05), this decrease was markedly less than that observed in Group I ACEI-treated rats, where average $P_{GC}$ decreased by 16 mm Hg. Whether inhibition of converting enzyme in the setting of previous antagonism of AII receptor had an additional independent effect on filtration was then examined.

ACEI following AIIRA caused a profound fall in the rate of filtration: GFR and SNGFR fell even below baseline (Table 1). Of note, the profound hypofiltration occurred in the face of renal dilatation. $Q_A$ increased further to 134±19 nl/min (p<0.025 vs. baseline), largely reflecting a marked decrease in the efferent arteriolar resistance. As in Group 1, this was associated with a precipitous decrease in $P_{GC}$, which was on average 15 mm Hg lower than baseline value.

Figure 2:
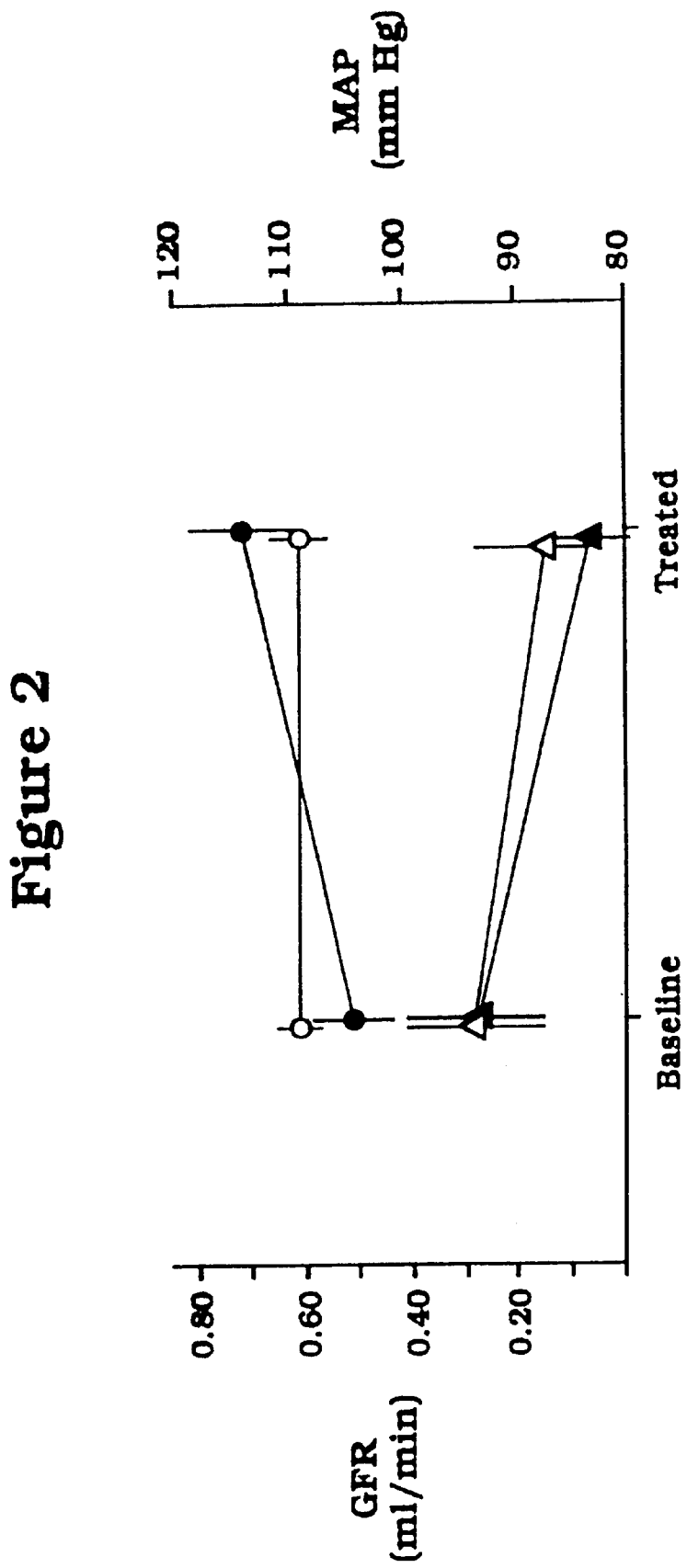
FIG. 2 shows mean arterial pressure (MAP) and glomerular filtration rate (GFR) in AWD rats treated with Furosemide. MAP decreased similarly in both ACEI, Group IIIA (Δ) and AIIRA, Group IIIB (▲). By contrast, GFR was unchanged with ACEI (○) and increased significantly with AIIRA (●).
Figure 3A:
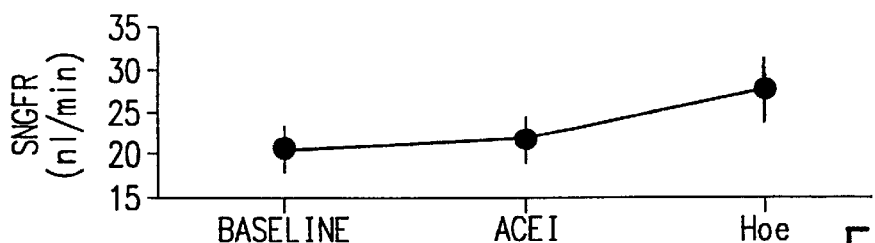
FIG. 3 is a summary of effects of ACEI and bradykinin antagonist (Hoe) in AWD+Furosemide Group IVA rats. The decrease in glomerular capillary pressure ($P_{GC}$) with ACEI was restored with Hoe, primarily reflecting elevation in efferent arteriolar resistance, $R_E$.
Figure 3B:
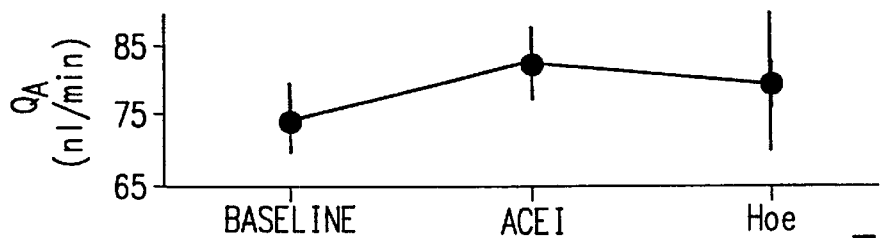
Figure 3C:
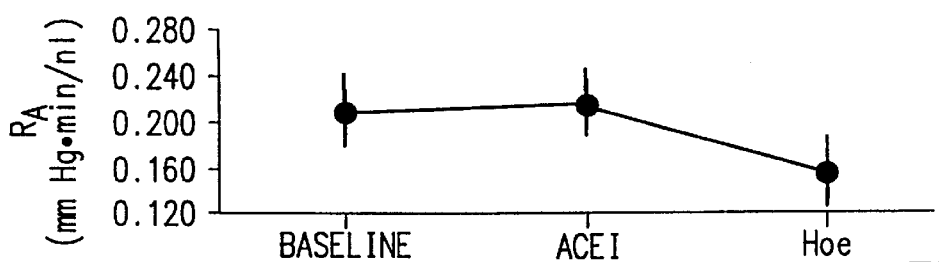
Figure 3D:
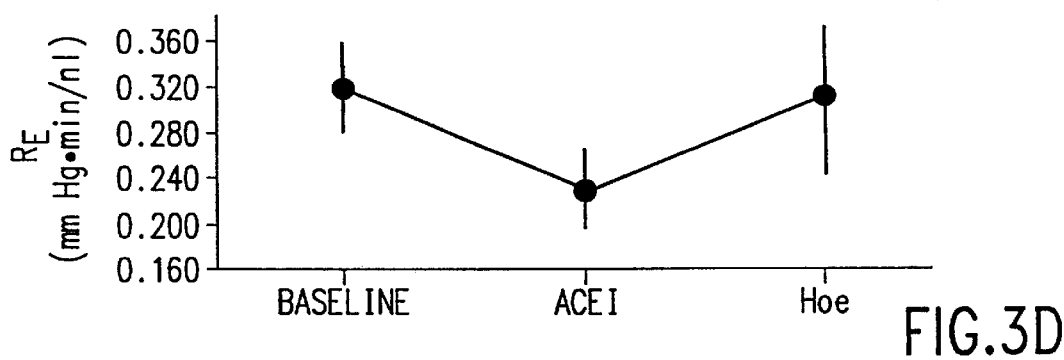
Figure 3E:
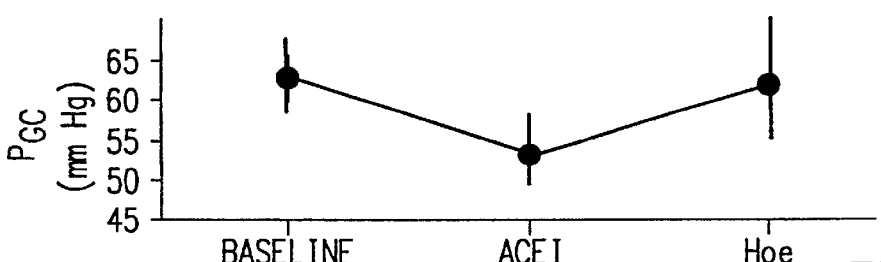

Groups IIIA and B, AWD+Furosemide, treated with ACEI or AIIRA. Due to the potential persisting actions of the long lasting AIIRA, separate groups of animals were treated with ACEI (Group IIIA) or AIIRA (Group IIIB). To confirm differences in renal microcirculatory responses to ACEI versus AIIRA under conditions with extreme stimulation of the RAS, these animals received furosemide in addition to AWD. Group III rats were more profoundly dehydrated than Groups I and II as evidenced by higher hematocrit (60±1% vs. 52±1 and 51±1, respectively, for Group III versus Group I and 2, p<0.0005). MAP decreased from baseline in both Groups IIIA and IIIB with treatment: 93±6 mm Hg to 87±5 (p<0.025), and 93±6 mm Hg to 83±3 (p<0.05), respectively (FIG. 2). Similar to Groups I and II, ACEI did not affect GFR (0.61±0.04 ml/min versus 0.61±0.05). In contrast to ACEI, inhibition of AII with receptor antagonist resulted in marked improvement in GFR which, on average, increased from 0.51±0.07 ml/min to 0.72±0.09 (p<0.01).

Group IVA and B, AWD+Furosemide, treated with ACEI and bradykinin receptor antagonist, Hoe (n=9) or Hoe (n=6). To further explore the mechanisms underlying these differing effects on the rate of glomerular filtration, we studied the potential contribution of bradykinin, as, ACEI, unlike AIIRA, acts as a kininase inhibitor. For this purpose, we evaluated the renal microcirculation in response to a specific bradykinin receptor antagonist. ACEI decreased MAP (98±3 mm Hg to 90±2) and increased renal perfusion without improving hypofiltration, GFR 0.50±0.08 ml/min versus 0.58±0.08, SNGFR 21±2 nl/min versus 22±2. The individual parameters are shown in FIG. 3, again emphasizing the marked decrease in $P_{GC}$ following ACEI (63±4 mm Hg vs. 53±3, p<0.005). The contribution of bradykinin was evaluated in the third period. MAP was unchanged from that during ACEI treatment. Filtration increased significantly; GFR rose to 0.71±0.10 ml/min (p<0.005 vs. ACEI), and SNGFR increased to 28±3 nl/min (p<0.05 vs. ACEI). This improvement in filtration was due to an increase in glomerular pressure which returned toward the baseline level (62±6 mm Hg, p<0.05 ACEI vs. Hoe), reflecting return of efferent arteriolar resistance to baseline levels, 0.312±0.050 mm Hg·min/nl. The value for $K_f$ was not affected by the bradykinin antagonist [1.735±0.320 nl/(min·mm Hg) vs. 1.465±0.472, ACEI vs. Hoe, respectively]. In Group IVB, AWD+furosemide animals treated with the bradykinin antagonist alone, GFR was 0.81±0.10 ml/min at baseline, with no significant change after bradykinin antagonist, 0.89±0.19 ml/min.

Separate rats were treated with either ACEI or AIIRA after prostaglandin inhibition with indomethacin. SNGFR showed ~20% increase over baseline after ACEI versus 100% increase after AIIRA (p<0.05), $Q_A$ increased ~70% versus ~140%, and $R_A$ decreased ~30% versus ~60% (p<0.05), respectively. These findings are taken to suggest that prostaglandins are not the major intermediary mechanism for the greater divergence between vasodilatation and perfusion seen after ACEI versus AIIRA.

The likelihood of achieving success in humans based on these specific findings in the rat is based on several facts. First, systemic and renal hemodynamics in normal and disease states have been investigated extensively in the rat and found to he relevant to clinical conditions in humans. Second, the RAS is phylogenetically tightly preserved, with activation in response to similar stimuli in both rats and humans, and the type 1 vascular receptor is found in both rats and humans with over 90% homology. Further, inhibition of the RAS by ACEI has been shown to have parallel effects in both rats and humans. Therefore, inhibition of RAS by the AII type 1 vascular receptor antagonist is expected to have the same effects in humans as shown in these rat studies.

The preceding examples are intended to illustrate but not limit the invention. While they are typical of those that might be used, other procedures known to those skilled in the art may be alternatively employed.

TABLE 1

Systemic and Renal Microcirculatory Parameters in AWD Rats in Response to Inhibition of the Renin Angiotensin System

| | MAP mmHg | GFR ml/min | SNGFR nl/min | $Q_A$ nl/min | $P_{GC}$ mmHg | $R_A$ mmHg · min/ml | $R_E$ mmHg · min/nl | $K_f$ nl/(min · mmHg) |
|---|---|---|---|---|---|---|---|---|
| Baseline | 95 ± 2 | 0.46 ± 0.07 | 25.2 ± 2.5 | 82 ± 7 | 67 ± 3 | 0.170 ± 0.015 | 0.333 ± 0.042 | 1.322 ± 0.368 |
| AIIRA | 88 ± 2* | 0.59 ± 0.05* | 30.2 ± 2.3* | 111 ± 21 | 60 ± 2* | 0.143 ± 0.023 | 0.240 ± 0.037* | 1.968 ± 0.311 |
| ACEI | 89 ± 2* | 0.41 ± 0.04‡ | 21.5 ± 1.1‡ | 134 ± 19* | 52 ± 1*‡ | 0.169 ± 0.016 | 0.159 ± 0.032* | 2.188 ± 0.381 |

AWD acute water deprivation;
MAP mean arterial pressure;
GFR whole kidney glomerular filtration rate;
SNGFR single nephron GFR;
$Q_A$ initial glomerular plasma flow rate;
$P_{GC}$ glomerular capillary hydraulic pressure;
$R_A$ afferent arteriolar resistance;
$R_E$ efferent arteriolar resistance;
$K_f$ glomerular capillary ultrafiltration coefficient.
*P < 0.05 vs. baseline;
‡P < 0.05 vs. AIIRA (specific P values in the text).

REFERENCES

1. Blantz, R. C., K. S. Konnen, and B. J. Tucker. 1976. Angiotensin II effects upon the glomerular microcirculation and ultrafiltration coefficient of the rat. *J. Clin. Invest.* 57: 419–434.
2. Clappison, B. H., W. P. Anderson, and C. I. Johnston. 1981. Renal hemodynamics and renal kinins after angiotensin converting enzyme inhibition. *Kidney Int.* 20: 615–620.
3. Navar, L. G., J. D., P. D. Bell, C. E. Thomas, and W. C. Huang. 1982. Influence of converting enzyme inhibition on renal hemodynamics in sodium-restricted dogs. *Hypertension.* 4: 58–68.
4. Rosivall, L. and L. G. Navar. 1983. Effects on renal hemodynamics of intra-arterial infusions of angiotensins I and II. *Am. J. Physiol.* 245: F181-F187.
5. Kastner, P. R., J. E. Hall, and A. C. Guyton. 1984. Control of glomerular filtration rate: Role of intrarenally formed angiotensin II. *Am. J. Physiol.* 246: F897-F906.
6. Kon, V., A. Yared, and I. Ichikawa. 1985. Role of renal sympathetic nerves in mediating hypoperfusion of renal cortical microcirculation in experimental congestive heart failure and acute extracellular fluid volume depletion. *J. Clin. Intest.* 76: 1913–1920.
7. Zusman, R. M. 1984. Renin- and non-renin-mediated antihypertensive actions of converting enzyme inhibitors. *Kidney Int.* 25: 969–983.
8. Scicli, A. G. and O. A. Carretero. 1986. Renal kallikrein-kinin system. *Kidney Int.* 29: 120–130.
9. Williams, G. H. 1988. Converting-enzyme inhibitors in the treatment of Hypertension. *N. Engl. J. Med.* 319: 1517–1525.
10. Gardes, J., T. Baussant, P. Corvol, J. Ménard, and F. Alhene-Gelas. 1990. Effect of bradykinin and kininogens in isolated rat kidney vasoconstricted by angiotensin II. *Am. J. Physiol.* 258: F1273-F1281.
11. Fenoy, F. J., G. Scicli, O. Carretero, and R. J. Roman. 1991. Effect of an angiotensin II and a kinin receptor antagonist on the renal hemodynamic response to captopril. *Hypertension.* 17: 1038–1044.
12. Hajj-ali, A. F. and B. G. Zimmerman. 1991. Kinin contribution to renal vasodilator effect of captopril in rabbit. *Hypertension.* 17: 504–509.
13. Mantlo, N. B., P. K. Chakravarty, D. Ondeyka, A. Chen, V. J. Camara, R. S. L. Chang, V. J. Lotti, P. K. S. Siegl, A. A. Patehett, and W. J. Greenlee. 1991. Potent, orally active imidazol[4,5-b]pyridine angiotensin II receptor antagonists. *J. Med. Chem.* 34: 2919–2922.
14. Siegl, P. K. S., R. S. L. Chang, N. B. Mantlo, P. K. Chakravarty, D. L. Ondeyka, W. J. Greenlee, A. A. Patehett, C. S. Sweet, and V. J. Lotti. In vivo pharmacology of L-158,809, a new highly potent and selective nonpeptide angiotensin II receptor antagonist. *J. Pharmacol. Exp. Therap.* In press.
15. Wirth, K, F. J. Hock, U. Albus, W. Linz, H. G. Alpermann, H. Anagnostopoulos, S. Henke, G. Breipohl, W. König, J. Knolle, and B. A. Schölkens. 1991. Hoe 140 a new potent and long acting bradykinin-antagonist: In vivo studies. *Br. J. Pharmacol.* 102: 774–777.
16. Yared, A, V. Kon, and I. Ichikawa. 1985. Mechanism of preservation of glomerular perfusion and filtration during acute extracellular fluid volume depletion. *J. Clin. Invest.* 75: 1477–1487.
17. Yoshioka, T., A. Yared, V. Kon, and I. Ichikawa. 1989. Impaired preservation of GFR during hypotension in preexistent renal hypoperfusion. *Am. J. Physiol.* 256: F314-F320.
18. Deen, W. M., J. L. Troy, C. R. Robertson, and B. M. Brenner. 1973. Dynamics of glomerular ultrafiltration in the rat IV. Determination of the ultrafiltration coefficient. *J. Clin. Invest.* 52: 1500–1508.
19. Deen, W. M., D. K Maddox, C. R. Robertson, B. M. Brenner, J. L. Troy, and I. F. Ueki. 1974. Dynamics of glomerular ultrafiltration in the rat. VII. Response to reduced renal mass. *Am. J. Physiol.* 227: 556–562.
20. Chang, R. S. L., P. K. S. Siegl, B. V. Clineschmidt, N. B. Mantlo, P. K Chaleravarty, W. J. Greenlee, A. A. Patehett, and V. J. Lotti. 1991. In vitro pharmacology of a highly potent and selective nonpeptide angiotensin II (AII) receptor antagonist: L-158,809. *FASEB J.* 5(Part III): 6993. (Abstr.)
21. Dzau, V. J., W. S. Colucci, G. H. Williams, G. Curfman, L. Meggs, and N. K. Hollenberg. 1980. Sustained effectiveness of converting-enzyme inhibition in patients with severe congestive heart failure. *N. Engl. J. Med.* 302: 1373–1379.
22. Hricik, D. E., P. J. Browning, R. Kopelman, W. E. Goorno, N. E. Madias, and V. J. Dzau. 1983. Captopril-induced functional renal insufficiency in patients with bilateral renal-artery stenoses or renal-artery stenosis in a solitary kidney. *N. Engl. J. Med.* 308: 373–376.
23. Packer, M., N. Medina, and M. Yushak. 1984. Efficacy of captopril in low-renin congestive heart failure: Importance of sustained reactive hyperreninemia in distinguishing responders from nonresponders. *Am. J. Cardiol.* 54: 771–777.
24. Ichikawa, I., J. M. Pfeffer, M. A. Pfeffer, T. H. Hostetter, and B. M. Brenner. 1984. Role of angiotensin II in the altered renal function of congestive heart failure. *Circ. Res.* 55: 669–675.
25. Murphy, B. F., J. A. Whitworth, and P. Kincaid-Smith. 1984. Renal insufficiency with combinations of angiotensin converting enzyme inhibitors and diuretics. *Brit. Med. J.* 288: 844–845.
26. Packer, M., W. H. Lee, M. Yushak, and N. Medina. 1986. Comparison of captopril and enalapril in patients with severe chronic heart failure. *N. Engl. J. Med.* 315: 847–853.
27. Packer, M., W. H. Lee, N. Medina, M. Yushak, and P. D. Kessler. 1987. Functional renal insufficiency during long-term therapy with captopril and enalapril in severe chronic heart failure. *Ann. Int. Med.* 106: 346–354.
28. McMurray, J. and D. M. Matthews. 1987. Consequences of fluid loss in patients treated with ACE inhibitors. *Postgrad. Med. J.* 63: 385–387.
29. Badr, K. F. and I. Ichikawa, 1988. Prerenal failure: A deleterious shift from renal compensation to decompensation. *N. Engl. J. Med* 319: 623–629.
30. Dzau, V. J. 1992. Angiotensin converting enzyme inhibitors and the cardiovascular system. *J. Hypertens.* 10: S3-S10.
31. Deedwania, P. C. 1990. Angiotensin-converting enzyme inhibitors in congestive heart failure. *Arch. Intern. Med.* 150: 1798–1805.
32. Whitebread, S., M. Mele, B. Kamber, and M. de Gasparo. 1989. Preliminary biochemical characterization of two angiotensin II receptor subtypes. *Biochem. Biophys. Res. Comm.* 163: 284–291.
33. Kakinuma, T., T. Inagami, A. Fogo, and I. Ichikawa. In situ hybridization studies of the intrarenal localization of angiotensin II type 1 receptor (AT1) mRNA in the rat. *J. Amer. Soc. Nephrol.* In press. (Abstr.)
34. Kohara, K., K. B. Brosnihan, C. M. Ferrario, and A. Milsted. 1992. Peripheral and central angiotensin II regulates expression of genes of the renin-angiotensin system. *Am. J. Physiol.* 262: E651-E657.
35. Campbell, D. J. 1987. Circulating and tissue angiotensin systems. *J. Clin. Invest.* 79: 1–6.
36. Aubert, J. F., B. Waeber, J. Nussberger, R. Vavrek, J. M. Stewart, and H. R. Brunner. 1987. Lack of a role of circulating bradykinin in the blood pressure response to acute angiotensin converting inhibition in rats. *Agents Actions.* 22: 349–354.
37. Camacho, A. A., M. C. O. Salgado, and E. M. Krieger. 1990. Reversal of hyperreactivity to bradykinin in renal hypertensive rats. *Hypertension.* 15(Suppl I): I140–I143.
38. Bao, G., P. Gohlke, F. Qadri, and T. Unger. 1992. Chronic kinin receptor blockade attenuates the antihypertensive effect of ramipril. *Hypertension.* 20: 74–79.
39. Edwards, R. M. 1985. Response of isolated renal arterioles to acetylcholine, dopamine, and bradykinin. *Am. J. Physiol.* 248:F183-F189.
40. Kakinuma, Y., T. Kawamura, T. Bills, T. Yoshioka, I. Ichikawa, and A. Fogo. 1992. Blood pressure-independent effect of angiotensin inhibition on vascular lesions of chronic renal failure. *Kidney Int.* 42:46–55.

What is claimed is:

1. A method of maintaining glomerular filtration rate while inhibiting mesangial matrix accumulation in a patient with hypoperfusion and hypofiltration with an activated renin-angiotensin system, comprising administering a matrix accumulation inhibiting amount of an angiotensin II type 1 vascular receptor antagonist to the patient.

2. The method of claim 1, wherein systemic blood pressure is lowered during the process of inhibiting mesangial matrix accumulation while maintaining glomerular filtration rate.

3. The method of claim 1, wherein the mesangial matrix accumulation inhibiting amount of angiotensin II type 1 vascular receptor antagonist administered is greater than the pressor dosage.

4. The method of claim 1, wherein the glomerular filtration rate relative to systemic blood pressure is increased from the hypertensive range after administration of angiotensin II type 1 vascular receptor antagonist.

5. The method of claim 1, wherein the glomerular filtration rate relative to systemic blood pressure is increased from the normal range after administration of the angiotensin II type 1 vascular receptor antagonist.

6. The method of claim 1, wherein angiotensin II type 1 receptor antagonist is L-158,809 (5,7-dimethyl-2-ethyl-3-[[2'-(1H-tetrazol-5yl)[1,1']-biphenyl-4-yl]-methyl]-3H-imidazo[4,5-b]pyridine).

7. A method of increasing glomerular filtration rate while inhibiting mesangial matrix accumulation in a patient with hypoperfusion and hypofiltration with an activated renin-angiotensin system, comprising administering a matrix accumulation inhibiting amount of an angiotensin II type 1 vascular receptor antagonist to the patient.

8. The method of claim 7, wherein systemic blood pressure is lowered during the process of inhibiting mesangial matrix accumulation while increasing glomerular filtration rate.

9. The method of claim 7, wherein the mesangial matrix accumulation inhibiting amount of angiotensin II type 1 vascular receptor antagonists administered is greater than the pressor dosage.

10. The method of claim 7, wherein the glomerular filtration rate relative to systemic blood pressure is increased from the hypertensive range after administration of angiotensin II type 1 vascular receptor antagonist.

11. The method of claim 7, wherein the glomerular filtration rate relative to systemic blood pressure is increased from the normal range after administration of the angiotensin II type 1 vascular receptor antagonist.

12. The method of claim 7, wherein angiotensin II type 1 receptor antagonist is L-158,809 (5,7-dimethyl-2-ethyl-3-[[2'-(1H-tetrazol-5yl)[1,1']-biphenyl-4-yl]-methyl]-3H-imidazo[4,5-b]pyridine).

* * * * *